(12) United States Patent
Date et al.

(10) Patent No.: US 8,953,862 B2
(45) Date of Patent: Feb. 10, 2015

(54) RADIATION DETECTION DATA PROCESSING APPARATUS AND METHOD RELATED TO COMPRESSION OF RADIATION DETECTION DATA

(75) Inventors: Naoto Date, Fukuoka (JP); Shinichiro Koto, Tokyo (JP); Hiroaki Nakai, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 96 days.

(21) Appl. No.: 13/595,228

(22) Filed: Aug. 27, 2012

(65) Prior Publication Data

US 2013/0058552 A1  Mar. 7, 2013

(30) Foreign Application Priority Data

Sep. 5, 2011 (JP) .................. 2011-192831

(51) Int. Cl.
  *G06K 9/00* (2006.01)
(52) U.S. Cl.
  CPC .................. *G06K 9/00* (2013.01)
  USPC ........................................... 382/131
(58) Field of Classification Search
  None
  See application file for complete search history.

(56) References Cited

U.S. PATENT DOCUMENTS

| | | | |
|---|---|---|---|
| 2004/0001611 A1* | 1/2004 | Celik et al. | 382/100 |
| 2004/0247070 A1* | 12/2004 | Ali et al. | 378/4 |
| 2008/0232542 A1* | 9/2008 | Lin | 378/16 |
| 2010/0070836 A1 | 3/2010 | Wegener et al. | |
| 2010/0278413 A1* | 11/2010 | Jarisch | 382/131 |
| 2011/0164678 A1* | 7/2011 | Date et al. | 375/240.03 |
| 2012/0207370 A1* | 8/2012 | Fahimian et al. | 382/131 |

FOREIGN PATENT DOCUMENTS

| | | |
|---|---|---|
| CN | 201500135 U | 6/2010 |
| JP | 2003-010170 | 1/2003 |
| WO | WO 2010/041488 A1 | 4/2010 |
| WO | WO2011/161558 * | 4/2011 |

OTHER PUBLICATIONS

Office Action mailed Jun. 5, 2014, in Chinese Patent Application No. 2012-10324288.9 (with English-language Translation).

* cited by examiner

*Primary Examiner* — Tahmina Ansari
(74) *Attorney, Agent, or Firm* — Oblon, Spivak, McClelland, Maier & Neustadt, L.L.P.

(57) ABSTRACT

According to one embodiment, a radiation detection data processing apparatus includes a data acquisition unit and a data processing unit. The data acquisition unit acquires a radiation detection data from a detector detecting radiation. The data processing unit generates a compressed data to be used for reconstruction of a tomographic image, compression distortion in the compressed data is nearly uniform independently of a signal value from the radiation detection data.

8 Claims, 15 Drawing Sheets

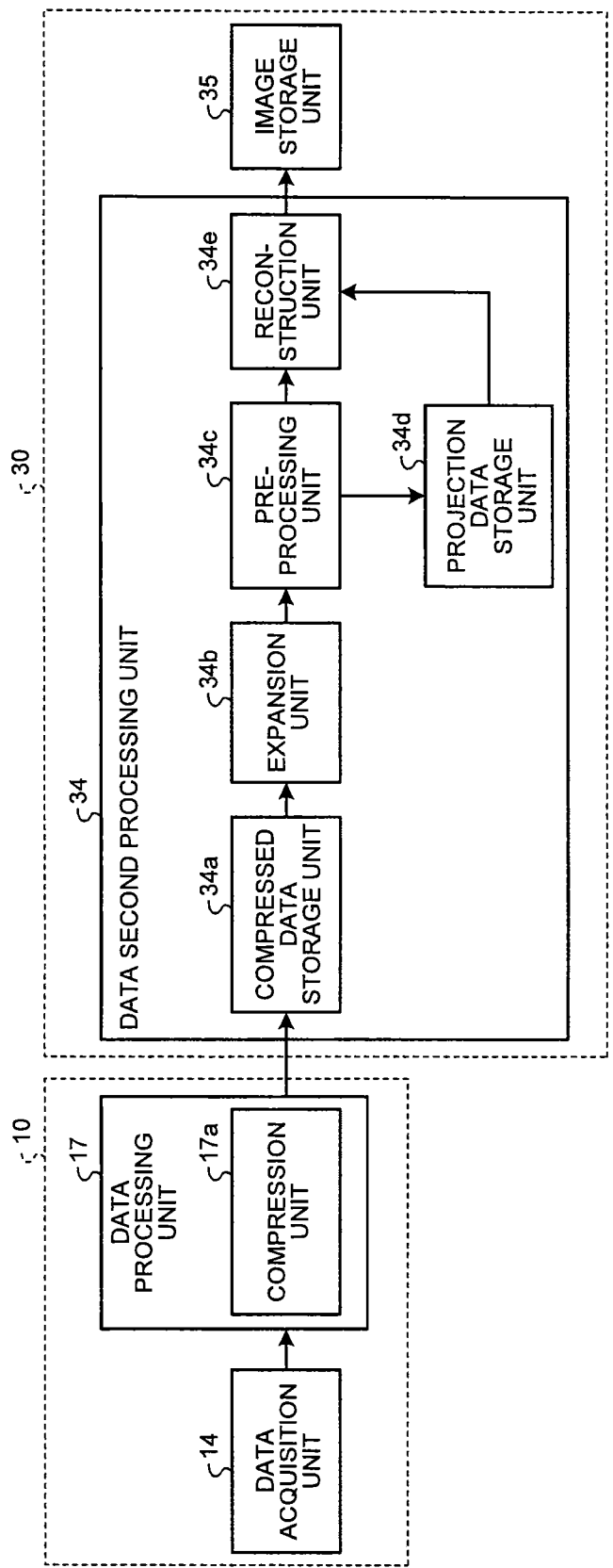

FIG.7A
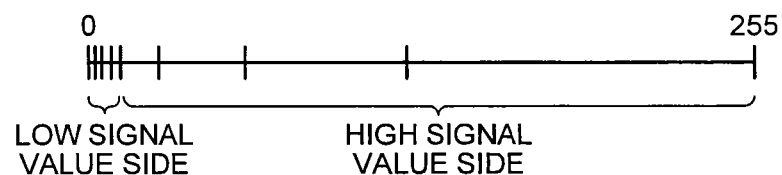
LOW SIGNAL VALUE SIDE    HIGH SIGNAL VALUE SIDE
FIG.7B
| | |
|---|---|
| 0 ≤ x ≤ 1 | 0 |
| 1 < x ≤ 3 | 2 |
| 3 < x ≤ 7 | 5 |
| 7 < x ≤ 15 | 10 |
| 15 < x ≤ 35 | 30 |
| 35 < x ≤ 75 | 55 |
| 75 < x ≤ 135 | 115 |
| 135 < x ≤ 255 | 200 |
FIG.8
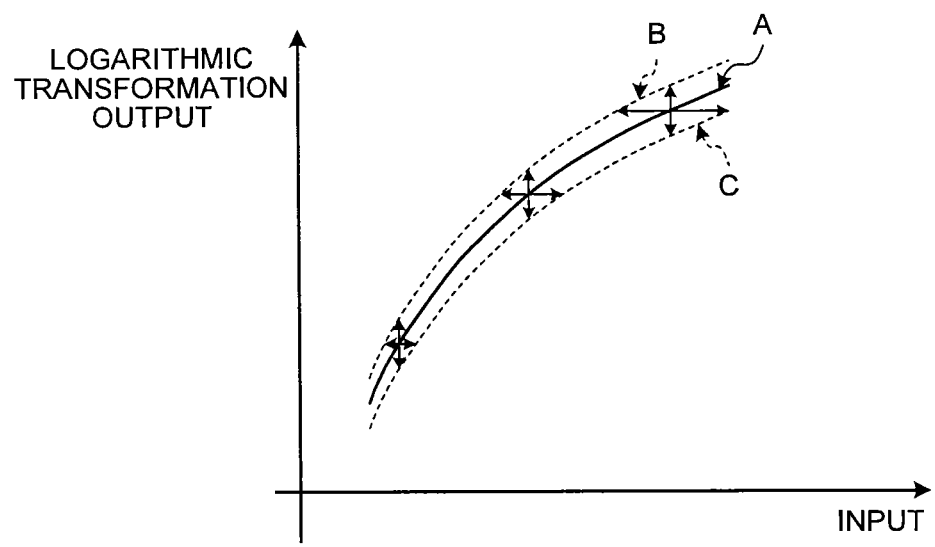

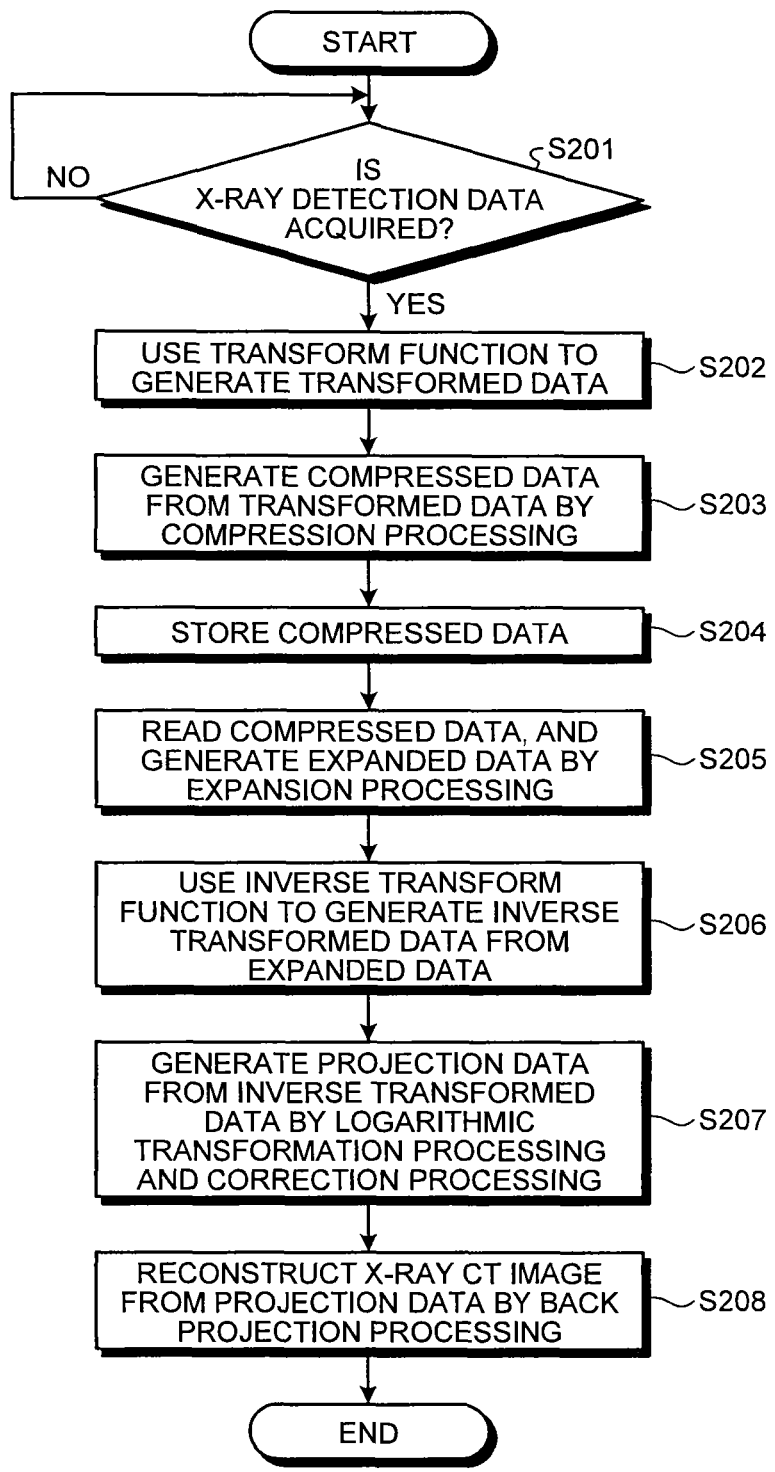

US 8,953,862 B2

RADIATION DETECTION DATA PROCESSING APPARATUS AND METHOD RELATED TO COMPRESSION OF RADIATION DETECTION DATA

CROSS-REFERENCE TO RELATED APPLICATIONS

This application is based upon and claims the benefit of priority from Japanese Patent Application No. 2011-192831, filed on Sep. 5, 2011; the entire contents of all of which are incorporated herein by reference.

FIELD

Embodiments described herein relate generally to a radiation detection data processing apparatus and a method.

BACKGROUND

Conventionally, computed tomography (CT) apparatuses that reconstruct a tomographic image of a test object have been in practical use in the medical field and non-destructive testing, for example. An X-ray CT apparatus, which is a CT apparatus, irradiates a test object with an X-ray in all directions of 360 degrees therearound, and detects the X-ray passing through the test object in each direction, for example. The X-ray CT apparatus then uses X-ray projection data obtained by performing logarithmic transformation and the like on X-ray detection data to reconstruct a tomographic image.

To obtain an accurate tomographic image, it is necessary to change the irradiation angle of the X-ray with high granularity and to use an X-ray detector in which X-ray detecting elements are arranged in high density. As a result, the resolution of the X-ray detection data and the number of images captured per unit time increase. To address these needs, there has been developed a technology for reducing costs for accumulation and transmission of X-ray detection data by compressing the X-ray detection data.

If X-ray detection data is compressed, the X-ray detection data thus compressed is expanded and then transformed logarithmically to generate X-ray projection data used for reconstruction of a tomographic image. In the data obtained by logarithmically transforming the data thus expanded, however, errors increase compared with data obtained by logarithmically transforming the X-ray detection data, resulting in degraded quality of the tomographic image.

BRIEF DESCRIPTION OF THE DRAWINGS

FIG. 6 is a schematic of configurations of a data processing unit and a data second processing unit according to the first embodiment;

FIGS. 7A and 7B are schematics of an example of compression processing according to the first embodiment;

FIG. 8 is a schematic for explaining a change of the compression distortion variance in the first embodiment;

FIG. 13 is a flowchart of processing performed by an X-ray CT apparatus according to the second embodiment;

DETAILED DESCRIPTION

According to one embodiment, a radiation detection data processing apparatus includes a data acquisition unit and a data processing unit. The data acquisition unit acquires a radiation detection data from a detector detecting radiation. The data processing unit generates a compressed data to be used for reconstruction of a tomographic image, compression distortion in the compressed data is nearly uniform independently of a signal value from the radiation detection data.

Exemplary embodiments of a radiation detection data processing apparatus are described below in greater detail with reference to the accompanying drawings. In the description below, X-ray computed tomography (CT) apparatuses including the radiation detection data processing apparatus will be explained as the embodiments.

First Embodiment

Figure 1:
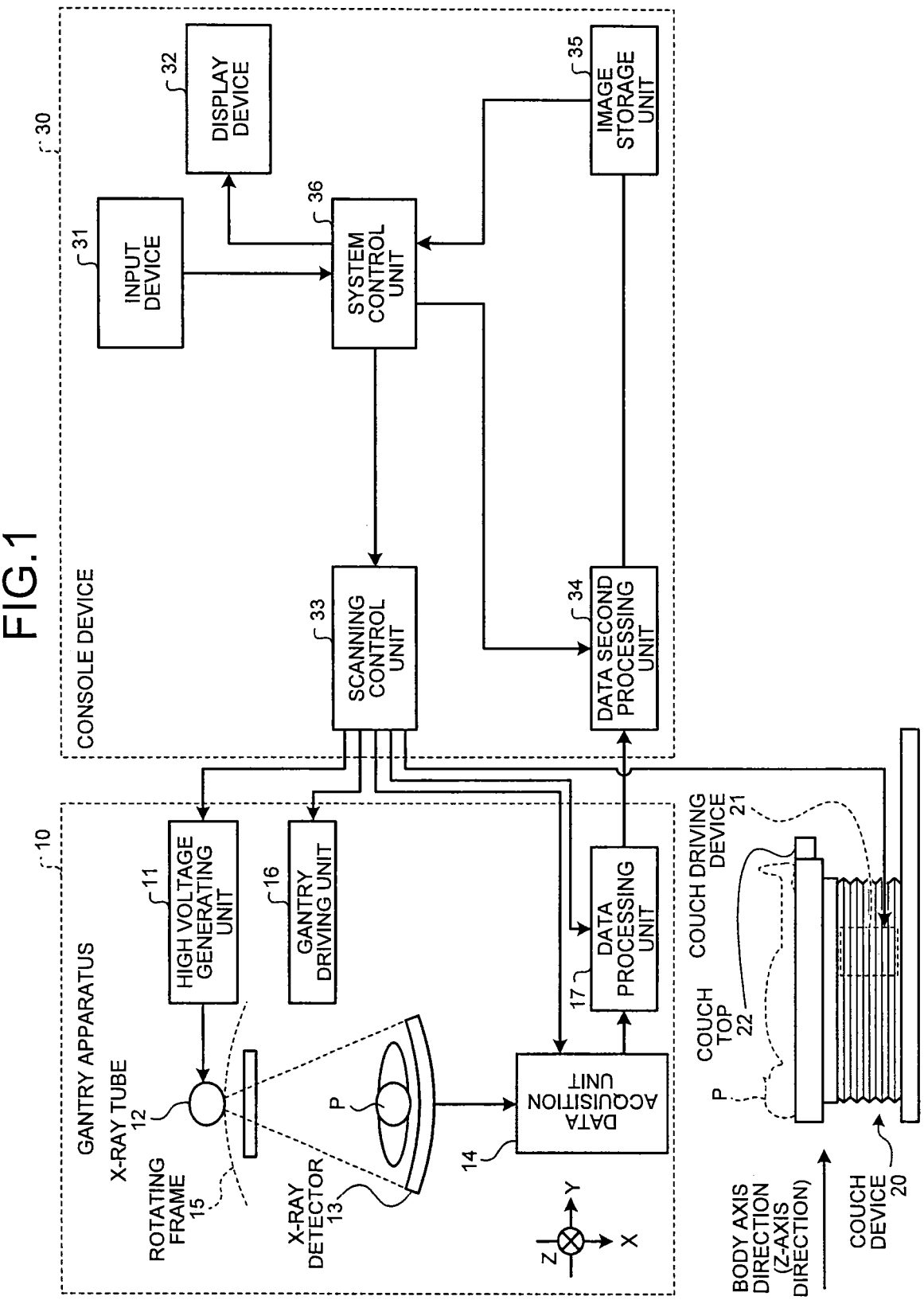
FIG. 1 is a schematic of an entire configuration of an X-ray CT apparatus according to a first embodiment.

An entire configuration of an X-ray CT apparatus according to a first embodiment will now be described with reference to FIG. 1. FIG. 1 is a schematic of the entire configuration of the X-ray CT apparatus according to the first embodiment. As illustrated in FIG. 1, the X-ray CT apparatus according to the first embodiment includes a gantry apparatus 10, a couch device 20, and a console device 30.

The gantry apparatus 10 is an apparatus that irradiates an X-ray to a subject P and then acquires X-ray detection data. The gantry apparatus 10 includes a high voltage generating unit 11, an X-ray tube 12, an X-ray detector 13, a data acquisition unit 14, a rotating frame 15, and a gantry driving unit 16. The gantry apparatus 10 further includes a data processing unit 17 that performs data processing on X-ray detection data.

The high voltage generating unit 11 is a device that generates a high voltage and supplies the high voltage thus generated to the X-ray tube 12. The X-ray tube 12 is a vacuum tube that generates an X-ray with the high voltage supplied from the high voltage generating unit 11, and the X-ray generated by the X-ray tube 12 is irradiated to a subject P.

The X-ray detector 13 is a detector that detects X-ray detection data indicating intensity distribution of the X-ray emitted from the X-ray tube 12 and passing through the subject P. In other words, the X-ray detector 13 detects X-ray detection data indicating the degree of X-ray absorption occurring in the subject P. Specifically, the X-ray detector 13 is a two-dimensional array detector in which a detecting element array composed of a plurality of X-ray detecting elements aligned in a channel direction (the Y-axis direction in FIG. 1) is aligned in plurality in a body-axis direction of the subject P (the Z-axis direction in FIG. 1).

The rotating frame 15 supports the X-ray tube 12 and the X-ray detector 13 in a manner facing each other with the subject P interposed therebetween. The gantry driving unit 16 is a driving device that drives to rotate the rotating frame 15, thereby causing the X-ray tube 12 and the X-ray detector 13 to rotate along a circular orbit about the subject P.

The data acquisition unit 14 is a data acquisition system (DAS), and acquires an X-ray detection data detected by the X-ray detector 13. Specifically, the data acquisition unit 14 acquires X-ray detection data corresponding to each irradiation direction of the X-ray emitted from the X-ray tube 12. The data acquisition unit 14 performs amplification, analog-digital (A/D) conversion, and the like on each X-ray detection data thus acquired, and outputs the X-ray detection data to the data processing unit 17.

The data processing unit 17 is a processing unit that performs predetermined data processing on X-ray detection data. Specifically, the data processing unit 17 performs compression processing on X-ray detection data, and transmits the data thus compressed to the console device 30, which will be described later. The processing performed by the data processing unit 17 in the first embodiment will be described later in detail.

The couch device 20 is a device on which the subject P is placed, and includes a couchtop 22 and a couch driving device 21 as illustrated in FIG. 1. The couchtop 22 is a bed on which the subject P is placed. The couch driving device 21 causes the couchtop 22 to move in the body-axis direction of the subject P (Z-axis direction), thereby moving the subject P into the rotating frame 15.

The console device 30 is a device that receives an operation for the X-ray CT apparatus performed by an operator and reconstructs a tomographic image from a projection data group acquired by the gantry apparatus 10. As illustrated in FIG. 1, the console device 30 includes an input device 31, a display device 32, a scanning control unit 33, a data second processing unit 34, an image storage unit 35, and a system control unit 36.

The input device 31 includes a mouse, a keyboard, a button, a trackball, a joystick, and the like used for inputting various types of instructions by the operator, such as a doctor and a technician, who operates the X-ray CT apparatus. The input device 31 transfers the various types of commands received from the operator to the system control unit 36, which will be described later.

The display device 32 includes a monitor that displays a graphical user interface (GUI) used for receiving the instructions from the operator via the input device 31 and that displays a reconstructed image stored in the image storage unit 35, which will be described later.

The scanning control unit 33 controls operations of the high voltage generating unit 11, the gantry driving unit 16, the data acquisition unit 14, the data processing unit 17, and the couch driving device 21. As a result, the scanning control unit 33 controls X-ray scanning performed on the subject P, acquisition of an X-ray detection data group, and data processing performed on the X-ray detection data group in the gantry apparatus 10.

Specifically, the scanning control unit 33 causes the X-ray tube 12 to emit an X-ray continuously or intermittently while rotating the rotating frame 15, thereby performing X-ray scanning. The scanning control unit 33, for example, performs helical scanning in which radiography is performed by rotating the rotating frame 15 continuously while moving the couchtop 22 and performs conventional scanning in which radiography is performed by rotating the rotating frame 15 once or continuously with the position of the subject P fixed.

The data second processing unit 34 is a processing unit that reconstructs a tomographic image (an X-ray CT image). In other words, the data second processing unit 34 uses data received from the data processing unit 17 to reconstruct an X-ray CT image. The image storage unit 35 stores therein the X-ray CT image generated by the data second processing unit 34. The processing performed by the data second processing unit 34 in the first embodiment will be described later in detail.

The system control unit 36 controls operations of the gantry apparatus 10, the couch device 20, and the console device 30, thereby controls the X-ray CT apparatus collectively. Specifically, the system control unit 36 controls the scanning control unit 33, thereby controlling acquisition of an X-ray detection data group performed by the gantry apparatus 10 and the couch device 20. The system control unit 36 controls the data processing unit 17 via the scanning control unit 33, thereby controlling compression processing performed on the X-ray detection data group. The system control unit 36 controls the data second processing unit 34, thereby controlling image reconstruction processing performed by the console device 30. The system control unit 36 performs control such that a reconstructed image is read from the image storage unit 35 and is displayed on the monitor included in the display device 32.

The explanation has been made of the entire configuration of the X-ray CT apparatus according to the first embodiment. With this configuration, the X-ray CT apparatus according to the first embodiment acquires X-ray detection data, and uses the X-ray detection data thus acquired to reconstruct an X-ray CT image.

Figure 2:
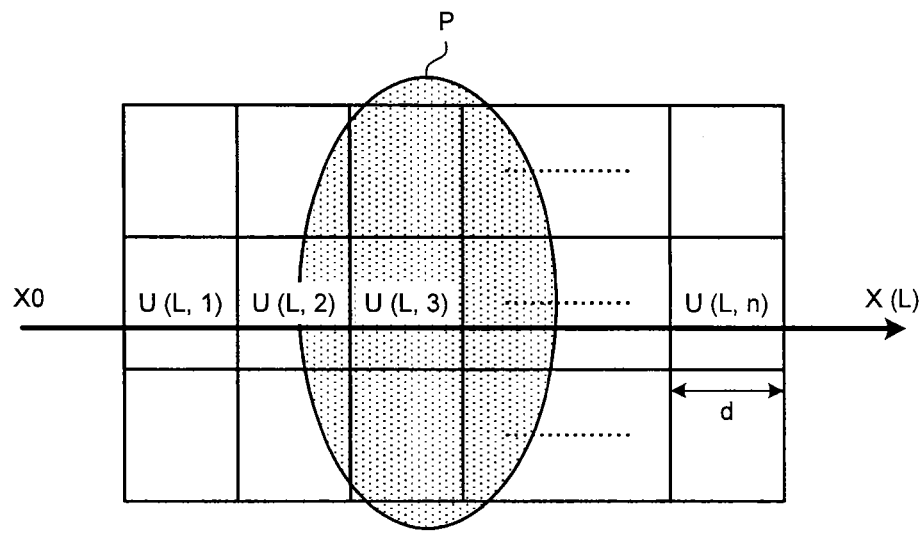
FIG. 2 is a schematic for explaining a method of reconstruction processing.

A method for reconstructing a tomographic image will now be described with reference to FIG. 2 and other figures. FIG. 2 is a schematic for explaining a method of reconstruction processing. FIG. 2 illustrates that the X-ray tube 12 emits an X-ray with X-ray intensity of "X0" at a certain X-ray irradiation angle. Furthermore, FIG. 2 illustrates that the X-ray detector 13 detects an X-ray with X-ray intensity of "X(L)" after the X-ray with X-ray intensity of "X0" passes through air represented by a white area in FIG. 2 and the subject P represented by a gray area in FIG. 2. In other words, in X-ray scanning, X-ray detection data "X(L)" of each penetrated radiation is acquired at every X-ray irradiation angle.

In FIG. 2, the space irradiated with the X-ray is divided in a mesh shape each of whose side length is "d", and an X-ray attenuation coefficient of each mesh is "U(L,n)". The X-ray intensity is attenuated exponentially on the penetrated radiation of the X-ray. With "X0", "d", and "U(L,n)", "X(L)" is calculated by Equation (1):

$$X(L) = X0 * e^{-\{U(L,1)+U(L,2)+\ldots+U(L,n)\}*d} \quad (1)$$

By taking logarithms of both sides, Equation (1) is expressed as Equation (2):

$$\log X(L) - \log(X0) = -\{U(L,1)+\ldots+U(L,n)\}*d \quad (2)$$

Because "X0", "X(L)", and "d" are already known, Equation (2) is the linear sum of an unknown "U". In other words, the X-ray CT apparatus acquires X-ray detection data "X(L)"

of each penetrated radiation at every X-ray irradiation angle, and transforms the X-ray detection data "X(L)" logarithmically, thereby obtaining Equation (2) composed of the linear sum related to the unknown "U". The data thus transformed logarithmically is referred to as projection data.

The X-ray CT apparatus then determines the unknown "U" from the projection data by using a least-squares method, a Fourier transform method, a filtered back projection method, a superimposed back projection method, and a iterative reconstruction method, for example, thereby obtaining each X-ray attenuation coefficient. In other words, the X-ray CT apparatus transforms the X-ray detection data logarithmically to generate projection data, and performs back projection of the projection data on the space irradiated with the X-ray, thereby obtaining an X-ray attenuation coefficient of each mesh in the space.

The X-ray CT apparatus then determines a CT value (unit: Hounsfield unit (HU)) obtained by relativizing the X-ray attenuation coefficient of each mesh with the X-ray attenuation coefficient of water "0" and the X-ray attenuation coefficient of air "−1000" to be a pixel value, thereby reconstructing an X-ray CT image.

Figure 3A:
FIGS. 3A and 3B are schematics for explaining reconstruction processing performed by a conventional X-ray CT apparatus.
Figure 3B:
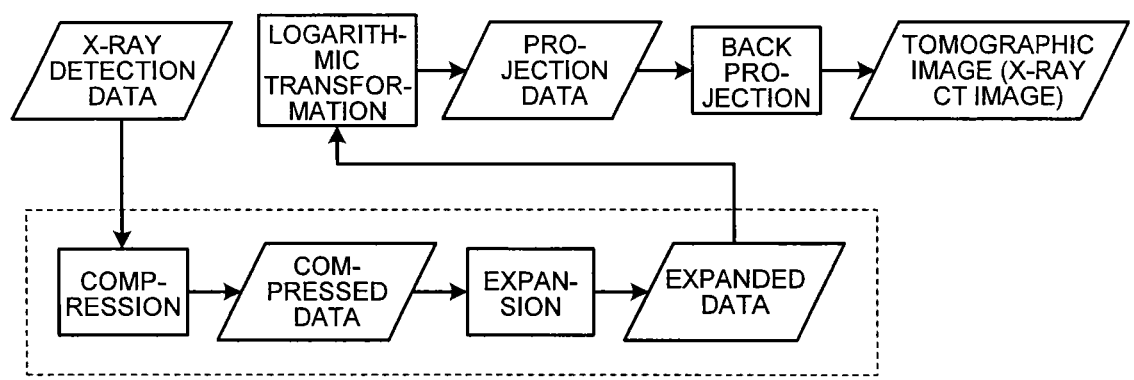

FIGS. 3A and 3B are schematics for explaining reconstruction processing performed by a conventional X-ray CT apparatus. As illustrated in FIG. 3A, for example, the conventional X-ray CT apparatus transforms acquired X-ray detection data logarithmically in the console device 30 as preprocessing prior to reconstruction, thereby generating projection data. The X-ray CT apparatus also performs correction processing, such as offset correction, sensitivity correction, and beam hardening correction, as the preprocessing in addition to the logarithmic transformation, thereby generating projection data from the X-ray detection data. The conventional X-ray CT apparatus then performs back projection of the projection data, thereby reconstructing a tomographic image (an X-ray CT image). The conventional X-ray CT apparatus illustrated in FIG. 3A stores the projection data in a predetermined storage unit, and reads the projection data thus stored to perform reconstruction processing.

To obtain a more accurate tomographic image, it is necessary to change the irradiation angle of an X-ray emitted from the X-ray tube 12 with high granularity and to use the X-ray detector 13 in which X-ray detecting elements are arranged in high density. In other words, to realize a high-definition tomographic image, the resolution of the X-ray detection data and the number of images captured per unit time increase. Therefore, to obtain a high-definition tomographic image, a high-speed transmission system and a device that stores therein a large volume of data are required.

To address this, conventionally known is an X-ray CT apparatus obtained by adding a data compression function to the X-ray CT apparatus illustrated in FIG. 3A. The conventional X-ray CT apparatus to which the data compression function is added compresses (encodes) X-ray detection data into compressed data as illustrated in FIG. 3B. The conventional X-ray CT apparatus illustrated in FIG. 3B, for example, creates data (sinogram data) by arranging X-ray detection data indicating an X-ray detection amount of each X-ray detecting element in chronological order for each X-ray irradiation angle, and compresses the sinogram data. The conventional X-ray CT apparatus illustrated in FIG. 3B then expands (decodes) the compressed data into expanded data, and performs processing, such as logarithmic transformation, on the expanded data to generate projection data. Subsequently, the conventional X-ray CT apparatus reconstructs a tomographic image (an X-ray CT image) by reconstruction processing.

By performing the compression processing in the gantry apparatus 10, for example, it is possible to reduce a transmission amount of data from the gantry apparatus 10 to the console device 30. Furthermore, by storing compressed data instead of projection data, a storage device provided to the console device 30 need not have large capacity.

Figure 4:
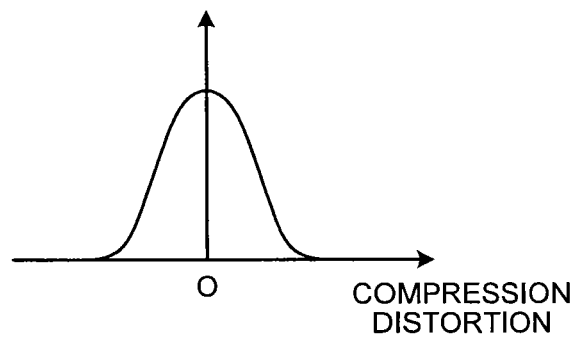
FIG. 4 is a schematic for explaining a distribution of the distortion caused by compression.
Figure 5:
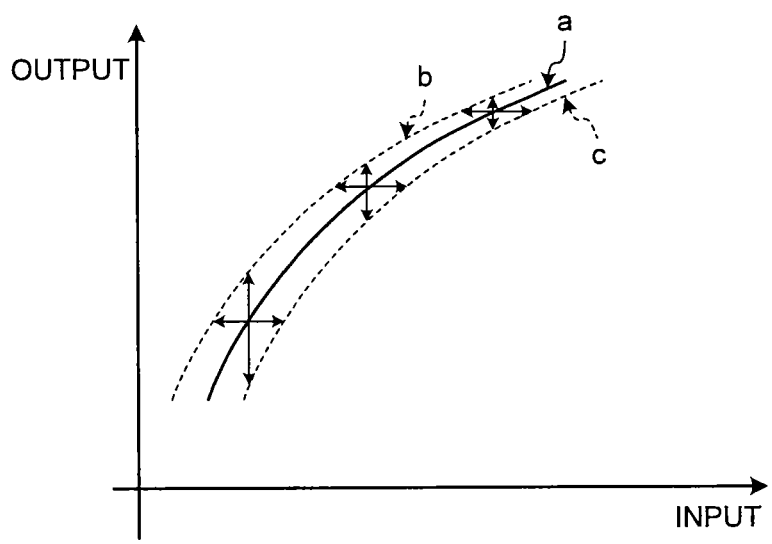
FIG. 5 is a schematic for explaining a change of the compression distortion variance caused by logarithmic transformation.

However, if the reconstruction processing is performed using the data obtained by logarithmically transforming the data thus compressed and expanded as the projection data, the quality of an image thus reconstructed may possibly be degraded. FIG. 4 is a schematic for explaining a distribution of the distortion caused by compression. FIG. 5 is a schematic for explaining a change of the compression distortion variance caused by logarithmic transformation.

While data to be compressed has inherent distortion caused by compression, such compression distortion has nearly uniform distribution regardless of signal intensity, and has an average value of "0" as illustrated in FIG. 4. In other words, by compressing X-ray detection data with a general method, compression distortion independent of the magnitude of signal values occurs in the compressed data. However, if expanded data is transformed logarithmically, the compression distortion becomes non-uniform depending on the magnitude of the signal values.

In FIG. 5, the horizontal axis represents signal values of expanded data serving as input, and the vertical axis represents signal values of logarithmically transformed data serving as output. In FIG. 5, a solid line a represents a graph plotting the signal values of input and output. Furthermore, in FIG. 5, a dotted line c represents a graph plotting the lower limit of compression distortion included in each signal value of the expanded data and a value obtained by transforming the lower limit logarithmically. Moreover, in FIG. 5, a dotted line b represents a graph plotting the upper limit of compression distortion included in each signal value of the expanded data and a value obtained by transforming the upper limit logarithmically.

The compression distortion in the expanded data of the input has a uniform distribution in the horizontal direction as indicated by the two-headed arrows in the horizontal direction in FIG. 5. By contrast, the compression distortion in the logarithmically transformed data of the output increases as the signal value becomes lower and decreases as the signal value becomes higher as indicated by the two-headed arrows in the vertical direction in FIG. 5.

Thus, the distribution of the compression distortion is changed by logarithmic transformation. In the data obtained by logarithmically transforming the data generated by compressing and expanding the X-ray detection data, error distribution relative to data obtained by logarithmically transforming the X-ray detection data increases as the signal value becomes lower. If such data is used for reconstruction processing, the calculation accuracy of the unknown "U" is reduced, thereby degrading the quality of a tomographic image.

To address this, the data processing unit 17 according to the first embodiment generates a compressed data to be used for reconstruction of a tomographic image, compression distortion in the compressed data is nearly uniform independently of a signal value from the X-ray detection data acquired by the data acquisition unit 14. The processing performed by the data processing unit 17 according to the first embodiment and by the data second processing unit 34 according to the first embodiment will now be described in detail with reference to FIG. 6 and other figures. FIG. 6 is a schematic of configurations of the data processing unit 17 and the data second processing unit 34 according to the first embodiment.

As illustrated in FIG. 6, the data processing unit 17 according to the first embodiment includes a compression unit 17a serving as a processing unit that generates a compressed data with which compression distortion in data to be used for reconstruction of a tomographic image is nearly uniform independently of signal values from X-ray detection data. The compression unit 17a generates the compressed data based on radiation detection data by using a quantization level at which compression distortion included in a lower signal value is smaller than compression distortion included in a higher signal value.

In other words, when performing compression processing, the compression unit 17a performs control to adjust the quantization level such that compression distortion included in a lower signal value is smaller than compression distortion included in a higher signal value so as to minimize error distribution included in logarithmically transformed data. When performing the compression processing by quantization and differential pulse code modulation (DPCM), for example, the compression unit 17a changes the quantization level depending on signal values. Specifically, the compression unit 17a adjusts the quantization level such that the quantization level becomes smaller as the signal value is smaller. FIGS. 7A and 7B are schematics of an example of the compression processing according to the first embodiment.

As illustrated in FIG. 7A, an assumption is made that a signal value (X) of the X-ray detection data is within a range of "$0 \leq x \leq 255$", for example. In this case, for example, the compression unit 17a determines the side on which x is closer to 0 to be a low signal value side, and determines the side on which x is closer to 255 to be a high signal value side. The compression unit 17a then sets eight quantization levels, for example.

As illustrated in FIG. 7B, for example, the compression unit 17a sets quantization levels of "$0 \leq x \leq 1$", "$1 < x \leq 3$", "$3 < x \leq 7$", "$7 < x \leq 15$", "$15 < x \leq 35$", "$35 < x \leq 75$", "$75 < x \leq 135$", and "$135 < x \leq 255$" from the low signal value side to the high signal value side.

The compression unit 17a then sets a representative value used for quantizing a signal value within the range of each quantization level. As illustrated in FIG. 7B, for example, the compression unit 17a sets the representative value of "$0 \leq x \leq 1$" to "0", sets the representative value of "$1 < x \leq 3$" to "2", sets the representative value of "$3 < x \leq 7$" to "5", sets the representative value of "$7 < x \leq 15$" to "10", sets the representative value of "$15 < x \leq 35$" to "30", sets the representative value of "$35 < x \leq 75$" to "55", sets the representative value of "$75 < x \leq 135$" to "115", and sets the representative value of "$135 < x \leq 255$" to "200".

In the example illustrated in FIGS. 7A and 7B, the quantization level decreases on the low signal value side, and increases on the high signal value side. Furthermore, in the example illustrated in FIGS. 7A and 7B, the compression unit 17a generates compressed data of 8 shades of gray from X-ray detection data of 256 shades of gray. In the compressed data, because the quantization level is set larger on the high signal value side, an error between the representative value and an actual measurement value is made larger on the high signal value side than on the low signal value side. By performing DPCM for obtaining the difference between signals adjacent to each other on the compressed data of 8 shades of gray, and performing variable-length coding on the differential signal thus obtained, compressed data further compressed is generated.

The compression unit 17a transmits the compressed data generated by the quantization level control to the data second processing unit 34 of the console device 30.

In the example illustrated in FIGS. 7A and 7B, the explanation has been made of the case where the X-ray detection data of 256 shades of gray is compressed into the data of 8 shades of gray before DPCM coding is performed. Alternatively, in the present embodiment, X-ray detection data of more shades of gray may be quantized depending on signal values. Furthermore, the quantization level may not be fixed but be variable in accordance with signal characteristics. To make the compression rate after the variable-length coding constant, for example, by quantizing an input signal roughly if the input signal has a large amount of information and quantizing an input signal finely if the input signal has a small amount of information, compressed data including information related to the quantization may be generated. At this time, a low signal value is quantized by a relatively smaller quantization level than a high signal value. Furthermore, the differential signal obtained by performing DPCM coding on the input signal value may be quantized. In this case, each block composed of a plurality of signal values may be encoded together with index information related to the quantization level such that the quantization level is adjusted depending on the magnitude of the input signal value, for example.

The ranges and the change of the quantization level set by the compression unit 17a may be set in advance, or may be set by the operator with the input device 31 during the radiography.

Referring back to FIG. 6, the data second processing unit 34 uses the compressed data received from the compression unit 17a to reconstruct an X-ray CT image. As illustrated in FIG. 6, the data second processing unit 34 according to the first embodiment includes a compressed data storage unit 34a, an expansion unit 34b, a preprocessing unit 34c, a projection data storage unit 34d, and a reconstruction unit 34e.

The compressed data storage unit 34a stores therein compressed data generated by the compression unit 17a. The expansion unit 34b generates expanded data by expanding compressed data. Specifically, the expansion unit 34b performs expansion processing on the compressed data stored in the compressed data storage unit 34a. The preprocessing unit 34c transforms the expanded data logarithmically, thereby generating projection data. Specifically, the preprocessing unit 34c performs correction processing, such as offset correction, sensitivity correction, and beam hardening correction, on the expanded data in addition to the logarithmic transformation, thereby generating projection data. The preprocessing unit 34c stores the projection data in the projection data storage unit 34d.

The reconstruction unit 34e performs back projection of the projection data generated by the preprocessing unit 34c transforming the expanded data logarithmically, thereby reconstructing an X-ray CT image, which is a tomographic image. The reconstruction unit 34e then stores the image thus reconstructed in the image storage unit 35. To perform the reconstruction processing, the reconstruction unit 34e may read the projection data from the projection data storage unit 34d, or may acquire the projection data from the preprocessing unit 34c.

In the first embodiment, the compressed data storage unit 34a stores therein compressed data. The volume of compressed data is smaller than that of projection data. Furthermore, storing of compressed data makes it possible to generate projection data at an arbitrary timing by expansion processing. Therefore, in the first embodiment, the projection data storage unit 34d may be omitted from the data second processing unit 34.

The compression distortion in the first embodiment will now be described with reference to FIG. 8. FIG. 8 is a schematic for explaining a change of the compression distortion variance in the first embodiment.

In FIG. 8, the horizontal axis represents "signal values of expanded data in the first embodiment" serving as input, and the vertical axis represents "signal values of data obtained by transforming the expanded data logarithmically" serving as output. In FIG. 8, a solid line A represents a graph plotting the signal values of input and output. Furthermore, in FIG. 8, a dotted line C represents a graph plotting "the lower limit of compression distortion included in each signal value of the expanded data in the first embodiment" and a value obtained by transforming the lower limit logarithmically. Moreover, in FIG. 8, a dotted line B represents a graph plotting "the upper limit of compression distortion included in each signal value of the expanded data in the first embodiment" and a value obtained by transforming the upper limit logarithmically.

In the compressed data generated in the first embodiment, the quantization level is controlled by the compression unit 17a such that the compression distortion increases as the signal value becomes higher. As a result, in the first embodiment, the compression distortion in the expanded data of the input decreases as the signal value becomes lower and increases as the signal value becomes higher as indicated by the two-headed arrows in the horizontal direction in FIG. 8. By contrast, the compression distortion in the logarithmically transformed data of the output has a nearly uniform distribution indicated by the two-headed arrows in the vertical direction in FIG. 8.

In other words, in the data obtained by transforming the expanded data logarithmically in the first embodiment, error distribution relative to data obtained by transforming the X-ray detection data logarithmically is reduced compared with the conventional compression processing. In the first embodiment, by using the data obtained by transforming the expanded data logarithmically for reconstruction processing, the unknown "U" can be calculated with high accuracy. As a result, it is possible to prevent image degradation of a tomographic image due to compression processing.

Figure 9:
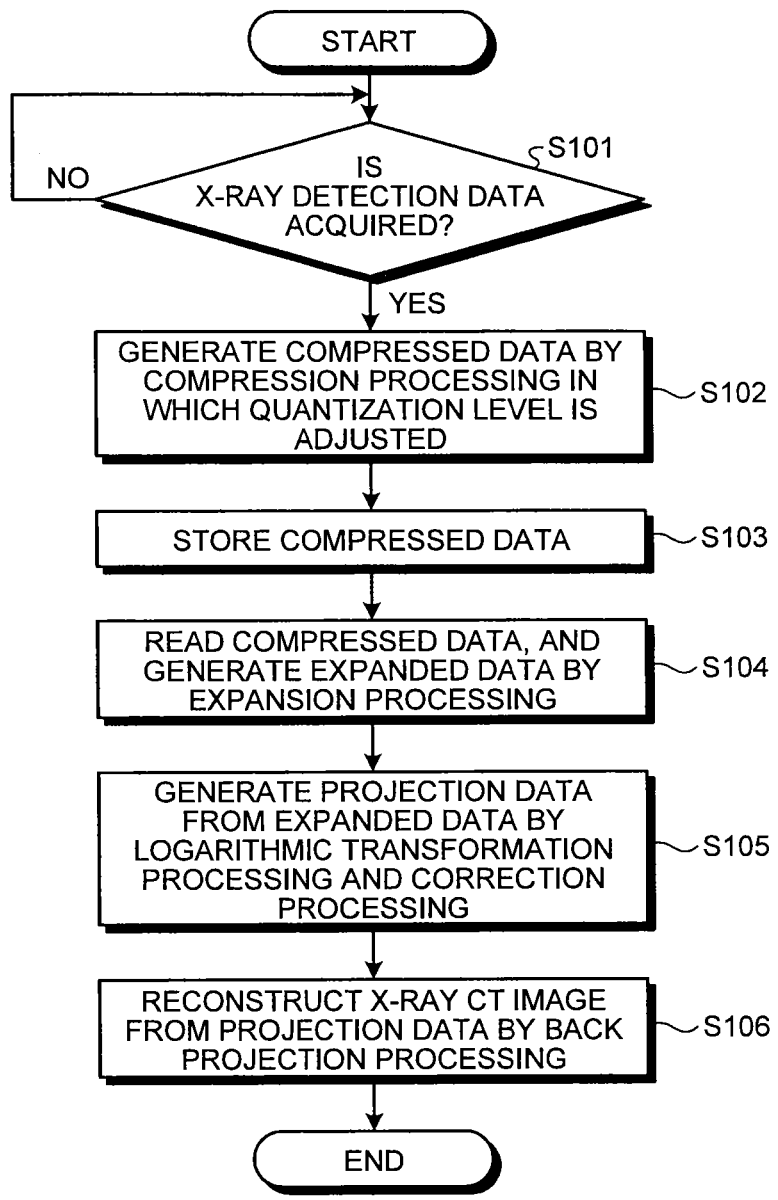
FIG. 9 is a flowchart of processing performed by the X-ray CT apparatus according to the first embodiment.

The processing performed by the X-ray CT apparatus according to the first embodiment will now be described with reference to FIG. 9. FIG. 9 is a flowchart of the processing performed by the X-ray CT apparatus according to the first embodiment.

As illustrated in FIG. 9, the X-ray CT apparatus according to the first embodiment determines whether the data acquisition unit 14 acquires X-ray detection data (Step S101). If no X-ray detection data is acquired (No at Step S101), the X-ray CT apparatus according to the first embodiment becomes in a standby mode.

By contrast, if X-ray detection data is acquired (Yes at Step S101), the compression unit 17a generates compressed data from the X-ray detection data by performing compression processing in which the quantization level is adjusted (Step S102). The compression unit 17a then transmits the compressed data to the console device 30 to store the compressed data in the compressed data storage unit 34a (Step S103).

Subsequently, the expansion unit 34b reads the compressed data from the compressed data storage unit 34a, and generates expanded data by performing expansion processing (Step S104). The preprocessing unit 34c generates projection data from the expanded data by performing logarithmic transformation processing and correction processing (Step S105). The reconstruction unit 34e reconstructs an X-ray CT image from the projection data by performing back projection processing (Step S106), and the processing is terminated.

As described above, in the first embodiment, controlling of the quantization level depending on signal values enables compression distortion in the data obtained by logarithmically transforming the expanded data to have nearly uniform distribution independently of the signal values. Therefore, in the first embodiment, it is possible to prevent image degradation of a tomographic image due to compression processing.

In the first embodiment, it is possible to transmit compressed data of X-ray detection data with which the quality of a tomographic image is not degraded. Therefore, no high-speed transmission system is required between the gantry apparatus 10 and the console device 30 for reconstruction of an accurate tomographic image. Furthermore, in the first embodiment, because compressed data is stored instead of a large volume of projection data, no device that stores therein a large volume of data is required. Moreover, in the first embodiment, because compressed data is stored, it is possible to newly reconstruct an image by arbitrarily changing reconstruction conditions, such as parameters used for the logarithmic transformation performed by the preprocessing unit 34c and the correction processing performed by the preprocessing unit 34c.

Figure 10:
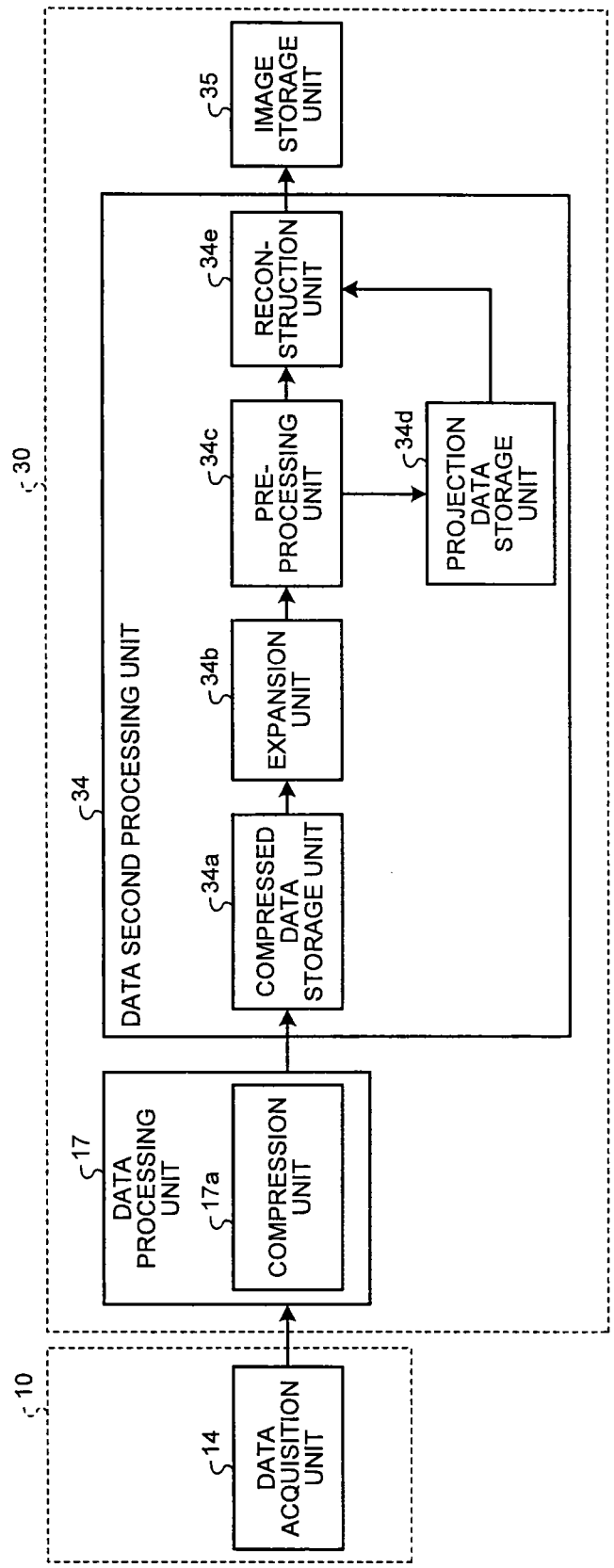
FIG. 10 is a schematic for explaining a modification of the first embodiment.

The explanation has been made of the case where the compression processing of the X-ray detection data is performed by the gantry apparatus 10. Alternatively, in the first embodiment, the compression processing of the X-ray detection data may be performed by the console device 30. FIG. 10 is a schematic for explaining a modification of the first embodiment.

As illustrated in FIG. 10, in the modification of the first embodiment, the data processing unit 17 including the compression unit 17a is provided to the console device 30. The compression unit 17a illustrated in FIG. 10 performs compression processing in which the quantization level is adjusted depending on signal values on X-ray detection data received from the gantry apparatus 10, thereby generating compressed data.

In the modification illustrated in FIG. 10, a device that stores therein data need not have large storage capacity in at least the console device 30 for reconstruction of an accurate tomographic image.

Second Embodiment

In a second embodiment, an explanation will be made of the case where a compressed data with which compression distortion in data to be used for reconstruction is nearly uniform independently of signal values is generated from X-ray detection data in a different manner from the first embodiment.

Figure 11:
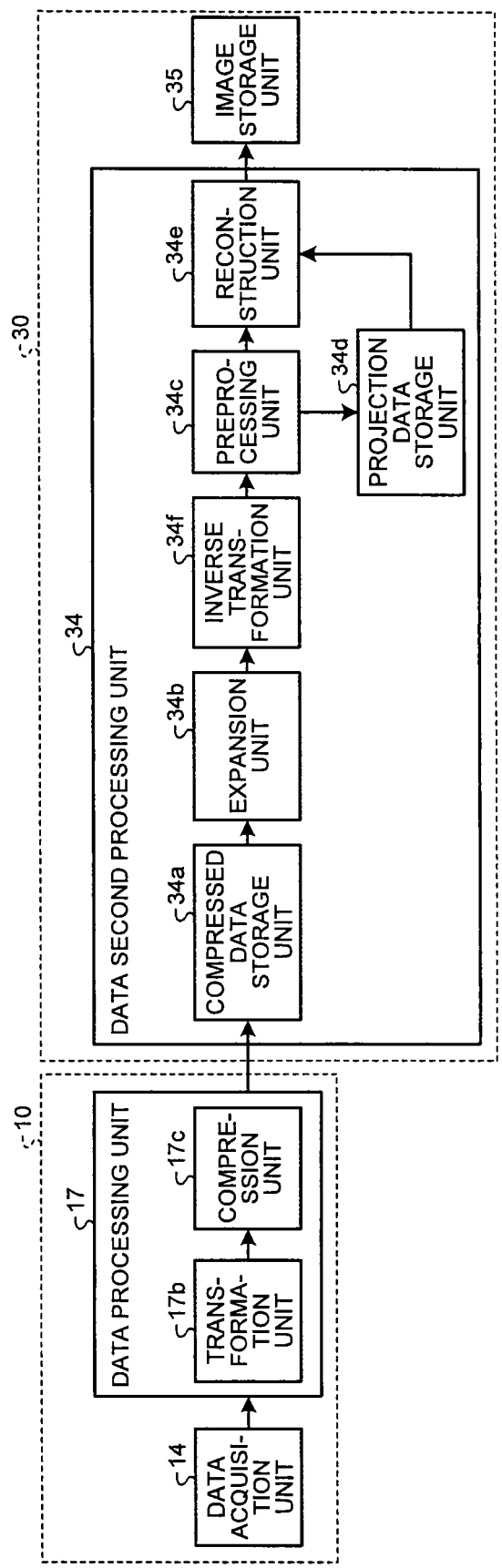
FIG. 11 is a schematic of configurations of a data processing unit and a data second processing unit according to a second embodiment.

An X-ray CT apparatus according to the second embodiment has the same configuration as that of the X-ray CT apparatus according to the first embodiment explained with reference to FIG. 1. However, configurations of the data processing unit 17 and the data second processing unit 34 according to the second embodiment are different from those in the first embodiment. FIG. 11 is a schematic of the configurations of the data processing unit 17 and the data second processing unit 34 according to the second embodiment. Also in the second embodiment, the data processing unit 17 generates a compressed data with which compression distortion in data to be used for reconstruction is nearly uniform independently of signal values from X-ray detection data in the same manner as in the first embodiment. However, the data processing unit 17 according to the second embodiment includes a transformation unit 17b and a compression unit 17c instead of the compression unit 17a.

The transformation unit 17b performs logarithmic transformation or approximate transformation that approximates the logarithmic transformation on the X-ray detection data to generate transformed data. FIGS. 12A to 12D are schematics for explaining the transformation processing according to the second embodiment.

Figure 12A:
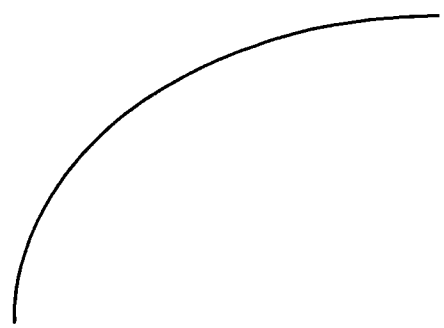
FIGS. 12A to 12D are schematics for explaining transformation processing according to the second embodiment.

As illustrated in FIG. 12A, for example, the transformation unit 17b uses a logarithmic function as a transform function to generate transformed data from the X-ray detection data. An output value obtained by logarithmically transforming a signal value on the X-ray detection data by using the logarithmic function is not necessarily 100% consistent with a logarithmic value of the signal value. The output value is an approximate value obtained by rounding up, rounding down, or rounding off the third decimal place, for example.

Alternatively, the transformation unit 17b generates transformed data from the X-ray detection data by using a transform function that approximates the logarithmic transformation. Specifically, the transformation unit 17b uses a transform function whose inclination decreases as the signal value becomes higher.

Figure 12B:
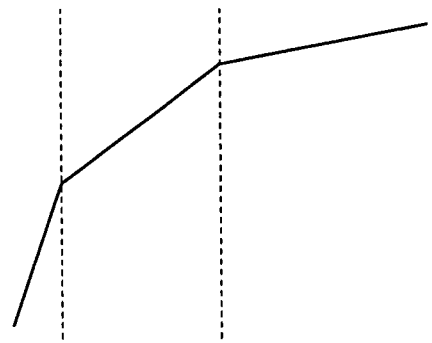

As illustrated in FIG. 12B, for example, the transformation unit 17b generates transformed data from the X-ray detection data by using a transform function that linearly approximates the whole logarithmic transformation. In the example illustrated in FIG. 12B, the transformation unit 17b divides the signal values into three ranges of a low signal value area, a medium signal value area, and a high signal value area, and uses three transform functions obtained by approximating logarithmic transformation in each range by a linear function. The inclinations of the transform functions decrease in order of the low signal value area, the medium signal value area, and the high signal value area as illustrated in FIG. 12B.

Figure 12C:
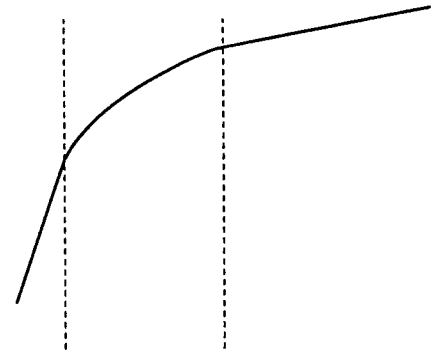

Alternatively, as illustrated in FIG. 12C, for example, the transformation unit 17b generates transformed data from the X-ray detection data by using a transform function that linearly approximates a part of the logarithmic transformation. In the example illustrated in FIG. 12C, the transformation unit 17b divides the signal values into three ranges of a low signal value area, a medium signal value area, and a high signal value area. The transformation unit 17b uses two transform functions obtained by approximating logarithmic transformation in the low signal value area and the high signal value area by a linear function, and uses a logarithmic function in the medium signal value area. The inclination (differential value) of the logarithmic function in the medium signal value area decreases compared with the inclination of the linear function in the low signal value area as illustrated in FIG. 12C. Furthermore, the inclination of the linear function in the high signal value area decreases compared with the inclination (differential value) of the logarithmic function in the medium signal value area as illustrated in FIG. 12C.

Figure 12D:
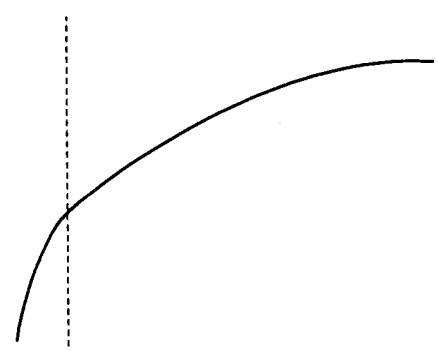

Still alternatively, as illustrated in FIG. 12D, for example, the transformation unit 17b generates transformed data from the X-ray detection data by using a transform function that approximates the whole logarithmic transformation by a polynomial. In the example illustrated in FIG. 12D, the transformation unit 17b divides the signal values into two ranges of a low signal value side and a high signal value side, and uses two transform functions obtained by approximating logarithmic transformation on the low signal value side and the high signal value side by a quadratic function. The inclination (differential value) of the quadratic function on the high signal value side decreases compared with the inclination (differential value) of the quadratic function on the low signal value side as illustrated in FIG. 12D.

The ranges and the transform functions used for the transformation processing performed by the transformation unit 17b may be set in advance, or may be set by the operator with the input device 31 during the radiography.

Referring back to FIG. 11, the compression unit 17c compresses the transformed data generated by the transformation unit 17b to generate compressed data. In other words, the compression unit 17c performs normal compression processing without performing adjustment of the quantization level explained in the first embodiment. The compression unit 17c then transmits the compressed data to the console device 30.

The data second processing unit 34 according to the second embodiment uses the compressed data received from the gantry apparatus 10 to reconstruct an X-ray CT image in the same manner as in the first embodiment. Similarly to the first embodiment, the data second processing unit 34 according to the second embodiment illustrated in FIG. 11 includes the compressed data storage unit 34a, the expansion unit 34b, a preprocessing unit 34c, the projection data storage unit 34d, and a reconstruction unit 34e. In addition, the data second processing unit 34 according to the second embodiment is provided with an inverse transformation unit 34f between the expansion unit 34b and the preprocessing unit 34c as illustrated in FIG. 11.

The compressed data storage unit 34a stores therein compressed data generated by the compression unit 17c. The expansion unit 34b generates expanded data by expanding compressed data. Specifically, the expansion unit 34b performs expansion processing on the compressed data stored in the compressed data storage unit 34a.

The inverse transformation unit 34f performs inverse transformation of the transformation performed by the transformation unit 17b on the expanded data to generate inverse transformed data. In other words, to perform inverse transformation of the transform function used by the transformation unit 17b, the inverse transformation unit 34f uses a function (inverse transform function) whose inclination increases as the signal value becomes higher, thereby generating inverse transformed data from the expanded data.

The preprocessing unit 34c performs logarithmic transformation processing and correction processing, such as offset correction, sensitivity correction, and beam hardening correction, on the inverse transformed data, thereby generating projection data. The reconstruction unit 34e performs back projection of the projection data generated by the preprocessing unit 34c transforming the inverse transformed data logarithmically, thereby reconstructing an X-ray CT image, which is a tomographic image. The reconstruction unit 34e then stores the image thus reconstructed in the image storage unit 35.

The expanded data according to the second embodiment includes compression distortion. In the second embodiment, however, no specific control of the quantization level or the like explained in the first embodiment is performed in the compression processing. As a result, the compression distortion in the expanded data according to the second embodiment is independent of the magnitude of signal values. By contrast, compression distortion included in the inverse transformed data is larger on the high signal value side than on the low signal value side because of inverse transformation performed by the inverse transformation unit 34f. In the second embodiment, by transforming the inverse transformed data logarithmically, projection data in which the compression distortion is independent of the magnitude of the signal values is generated.

In other words, in the data obtained by transforming the inverse transformed data logarithmically in the second embodiment, error distribution relative to data obtained by transforming the X-ray detection data logarithmically is reduced compared with the conventional compression processing. In the second embodiment, by using the data obtained by transforming the inverse transformed data logarithmically for reconstruction processing, it is possible to prevent image degradation of a tomographic image due to compression processing.

Also in the second embodiment, because the compressed data storage unit 34a stores therein compressed data, the projection data storage unit 34d may be omitted from the data second processing unit 34.

The processing performed by the X-ray CT apparatus according to the second embodiment will now be described with reference to FIG. 13. FIG. 13 is a flowchart of the processing performed by the X-ray CT apparatus according to the second embodiment.

As illustrated in FIG. 13, the X-ray CT apparatus according to the second embodiment determines whether the data acquisition unit 14 acquires X-ray detection data (Step S201). If no X-ray detection data is acquired (No at Step S201), the X-ray CT apparatus according to the second embodiment becomes in a standby mode.

By contrast, if X-ray detection data is acquired (Yes at Step S201), the transformation unit 17b uses a transform function to generate transformed data from the X-ray detection data (Step S202), and the compression unit 17c generates compressed data from the transformed data by performing compression processing (Step S203). The compression unit 17c then transmits the compressed data to the console device 30 to store the compressed data in the compressed data storage unit 34a (Step S204).

Subsequently, the expansion unit 34b reads the compressed data from the compressed data storage unit 34a, and generates expanded data by performing expansion processing (Step S205). The inverse transformation unit 34f uses an inverse transform function to generate inverse transformed data from the expanded data (Step S206). The preprocessing unit 34c generates projection data from the inverse transformed data by performing logarithmic transformation processing and correction processing (Step S207). The reconstruction unit 34e reconstructs an X-ray CT image from the projection data by performing back projection processing (Step S208), and the processing is terminated.

As described above, in the second embodiment, logarithmic transformation or transformation that approximates the logarithmic transformation is performed on the X-ray detection data in advance before the compression processing is performed. Therefore, the compression distortion in the expanded data obtained by expanding the compressed data has nearly uniform distribution independently of the magnitude of signal values.

In the second embodiment, inverse transformation is performed on the expanded data in which the compression distortion is nearly uniform, thereby generating inverse transformed data in which the compression distortion is larger on the high signal value side than on the low signal value side. In the second embodiment, by transforming the inverse transformed data logarithmically, the compression distortion in the data to be used for reconstruction processing is made nearly uniform.

As described above, in the second embodiment, data required to be subjected to logarithmic transformation again is generated from the expanded data that has already been subjected to processing corresponding to logarithmic transformation by the inverse transformation. In the second embodiment, by performing the inverse transformation, the conventional preprocessing unit 34c can be used without changing the function thereof.

In the second embodiment, it is possible to transmit compressed data of X-ray detection data with which the quality of a tomographic image is not degraded. Therefore, neither a high-speed transmission system nor a device that stores therein a large volume of data is required for reconstruction of an accurate tomographic image. Furthermore, in the second embodiment, because compressed data is stored, it is possible to newly reconstruct an image by arbitrarily changing reconstruction conditions, such as parameters used for the logarithmic transformation performed by the preprocessing unit 34c and the correction processing performed by the preprocessing unit 34c.

Figure 14:
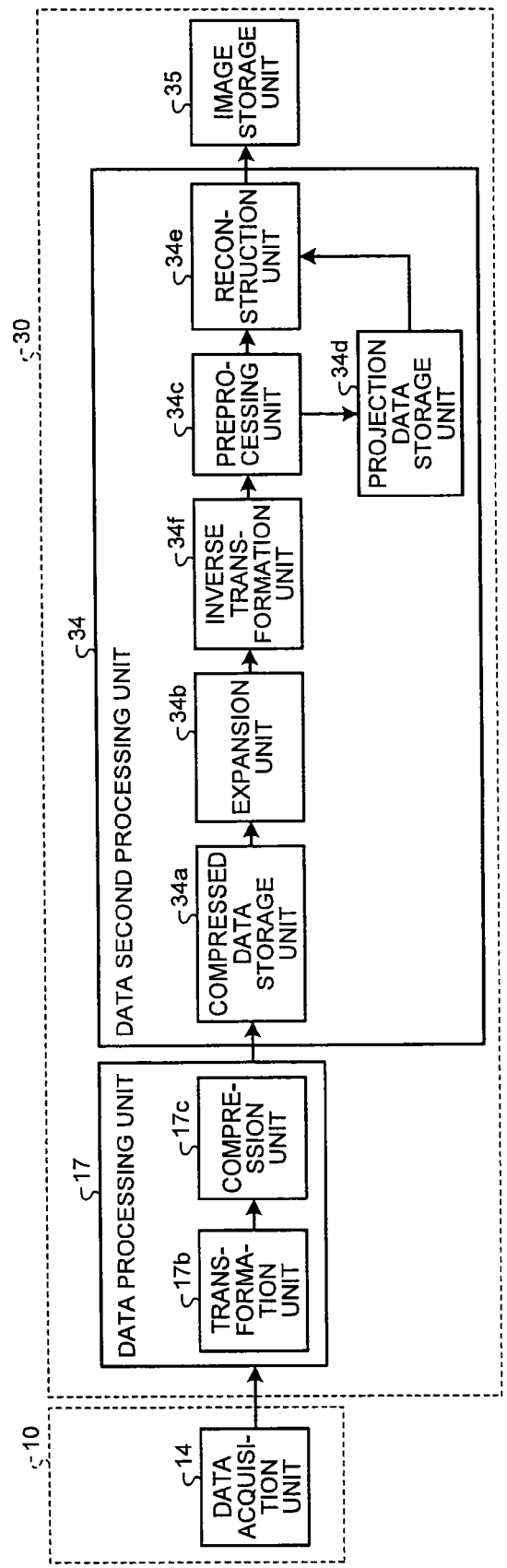
FIG. 14 is a schematic for explaining a modification of the second embodiment.

The explanation has been made of the case where the transformation processing and the compression processing of the X-ray detection data are performed by the gantry apparatus 10. Alternatively, in the second embodiment, the transformation processing and the compression processing of the X-ray detection data may be performed by the console device 30. FIG. 14 is a schematic for explaining a modification of the second embodiment.

As illustrated in FIG. 14, in the modification of the second embodiment, the data processing unit 17 including the transformation unit 17b and the compression unit 17c is provided to the console device 30. The transformation unit 17b illustrated in FIG. 14 uses a transform function for X-ray detection data received from the gantry apparatus 10 to generate transformed data. The compression unit 17c then performs compression processing on the transformed data, thereby generating compressed data.

In the modification illustrated in FIG. 14, a device that stores therein data need not have large storage capacity in at least the console device 30 for reconstruction of an accurate tomographic image.

Third Embodiment

In a third embodiment, an explanation will be made of the case where the inverse transformation described in the second embodiment is not performed.

Figure 15:
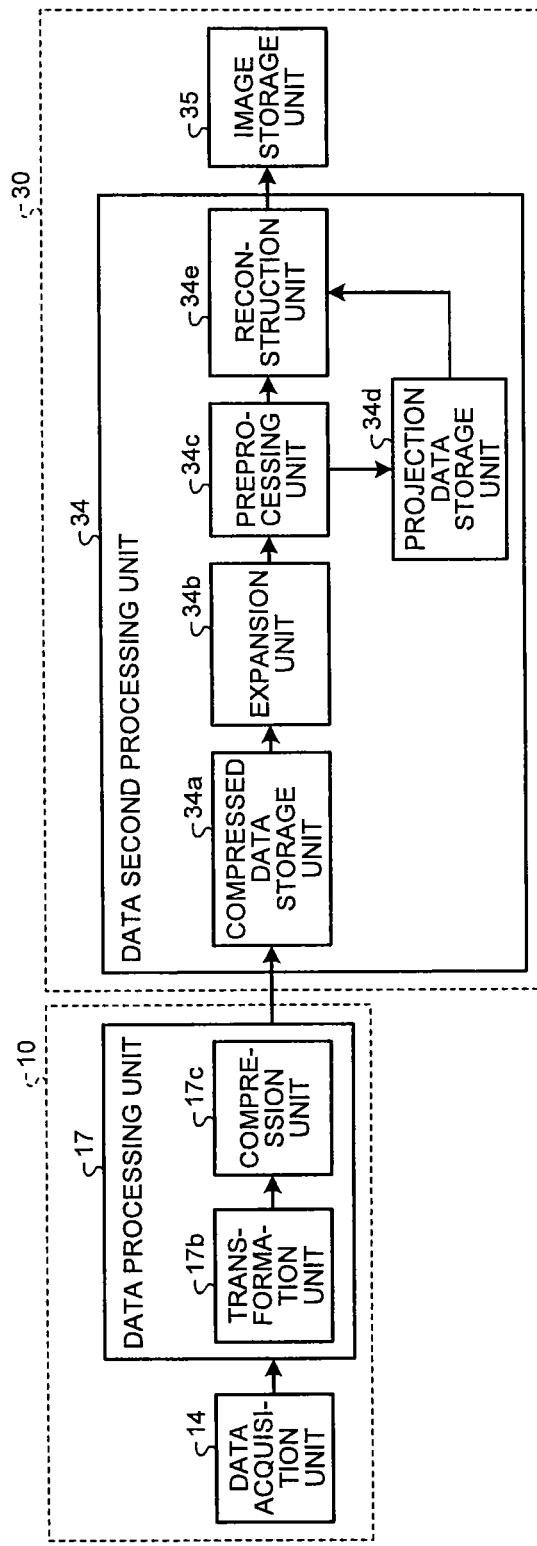
FIG. 15 is a schematic of configurations of a data processing unit and a data second processing unit according to a third embodiment.

An X-ray CT apparatus according to the third embodiment has the same configuration as that of the X-ray CT apparatuses according to the first and the second embodiments (refer to FIG. 1). However, a data processing unit 17 and a data second processing unit 34 according to the third embodiment are different from the data processing unit 17 and the data second processing unit 34 according to the second embodiment in that the inverse transformation unit 34f is omitted and that a preprocessing unit 34c only performs correction processing. FIG. 15 is a schematic of configurations of the data processing unit 17 and the data second processing unit 34 according to the third embodiment.

The data processing unit 17 according to the third embodiment illustrated in FIG. 15 generates compressed data with which compression distortion in data to be used for reconstruction is nearly uniform independently of signal values from X-ray detection data in the same manner as in the first and the second embodiments. As illustrated in FIG. 15, the data processing unit 17 according to the third embodiment includes the transformation unit 17b and the compression unit 17c. The transformation unit 17b illustrated in FIG. 15 performs logarithmic transformation or approximate transformation that approximates the logarithmic transformation on the X-ray detection data to generate transformed data in the same manner as in the second embodiment (refer to FIGS. 12A to 12D). The compression unit 17c illustrated in FIG. 15 compresses the transformed data to generate compressed data in the same manner as in the second embodiment. The compression unit 17c then transmits the compressed data to the console device 30.

The data second processing unit 34 according to the third embodiment uses the compressed data received from the gantry apparatus 10 to reconstruct an X-ray CT image in the same manner as in the first and the second embodiments. Similarly to the second embodiment, the data second processing unit 34 according to the third embodiment illustrated in FIG. 15 includes a compressed data storage unit 34a, an expansion unit 34b, a preprocessing unit 34c, a projection data storage unit 34d, and a reconstruction unit 34e. However, the data second processing unit 34 according to the third embodiment illustrated in FIG. 15 includes no inverse transformation unit 34f.

The compressed data storage unit 34a stores therein compressed data generated by the compression unit 17c. The expansion unit 34b generates expanded data by expanding compressed data. Specifically, the expansion unit 34b performs expansion processing on the compressed data stored in the compressed data storage unit 34a.

Similarly to the second embodiment, the expanded data according to the third embodiment is obtained by transforming data generated by compressing transformed data on which logarithmic transformation or approximate transformation of the logarithmic transformation is performed. Furthermore, in the third embodiment, no specific control of the quantization level or the like explained in the first embodiment is performed in the compression processing. As a result, the compression distortion in the expanded data according to the third embodiment is independent of the magnitude of signal values similarly to the second embodiment.

In the third embodiment, reconstruction processing is performed by using the expanded data. In other words, in the third embodiment, the reconstruction processing is performed by using the expanded data as data nearly identical to the data obtained by transforming X-ray detection data logarithmically.

The preprocessing unit 34c only performs correction processing, such as offset correction, sensitivity correction, and beam hardening correction, on the expanded data. The reconstruction unit 34e performs back projection of the expanded data, that is, the expanded data thus corrected, thereby reconstructing an X-ray CT image, which is a tomographic image. The reconstruction unit 34e then stores the image thus reconstructed in the image storage unit 35. In the third embodiment, the reconstruction unit 34e may perform the reconstruction processing by using the expanded data without the correction processing performed by the preprocessing unit 34c.

As described above, in the third embodiment, by using the expanded data in which the compression distortion is independent of the magnitude of signal values and that is nearly identical to the data obtained by transforming X-ray detection data logarithmically for the reconstruction processing, it is possible to prevent image degradation of a tomographic image due to compression processing.

Also in the third embodiment, because the compressed data storage unit 34a stores therein compressed data, the projection data storage unit 34d may be omitted from the data second processing unit 34.

Figure 16:
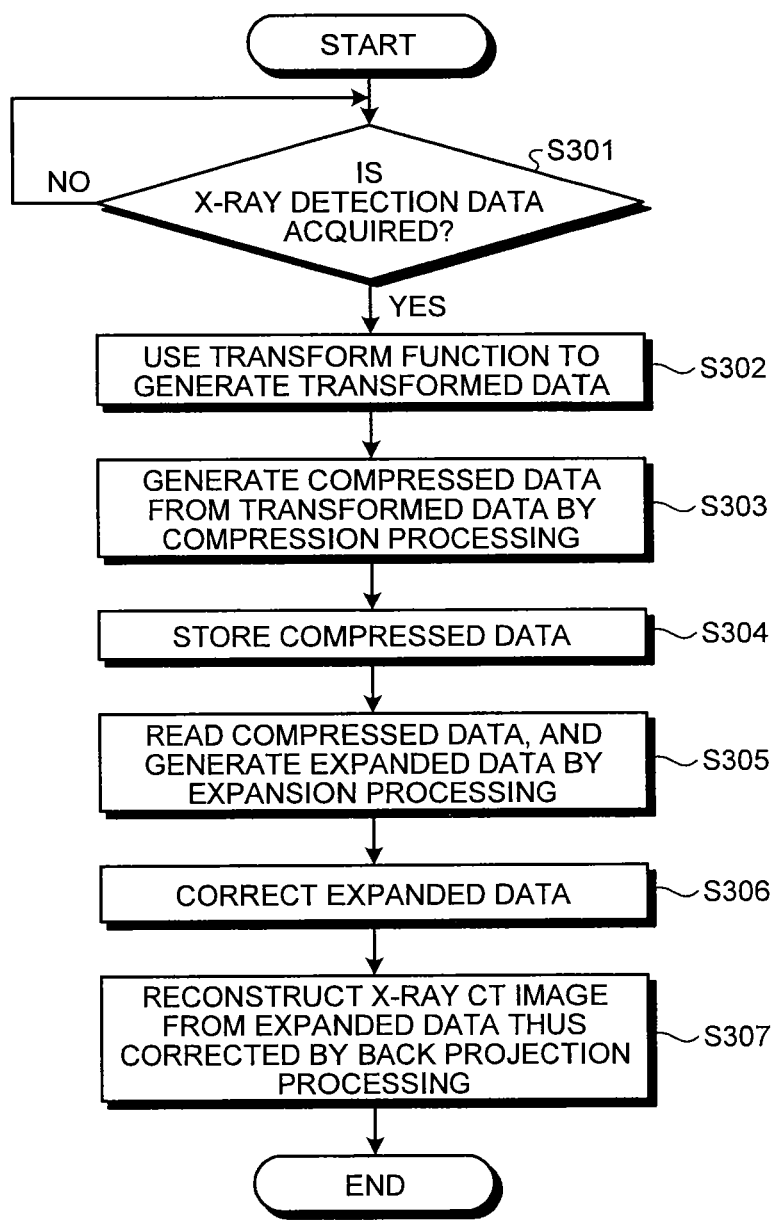
FIG. 16 is a flowchart of processing performed by an X-ray CT apparatus according to the third embodiment.

The processing performed by the X-ray CT apparatus according to the third embodiment will now be described with reference to FIG. 16. FIG. 16 is a flowchart of the processing performed by the X-ray CT apparatus according to the third embodiment.

As illustrated in FIG. 16, the X-ray CT apparatus according to the third embodiment determines whether a data acquisition unit 14 acquires X-ray detection data (Step S301). If no X-ray detection data is acquired (No at Step S301), the X-ray CT apparatus according to the third embodiment becomes in a standby mode.

By contrast, if X-ray detection data is acquired (Yes at Step S301), the transformation unit 17b uses a transform function to generate transformed data from the X-ray detection data (Step S302), and the compression unit 17c generates compressed data from the transformed data by performing compression processing (Step S303). The compression unit 17c then transmits the compressed data to the console device 30 to store the compressed data in the compressed data storage unit 34a (Step S304).

Subsequently, the expansion unit 34b reads the compressed data from the compressed data storage unit 34a, and generates expanded data by performing expansion processing (Step S305). The preprocessing unit 34c performs correction processing of the expanded data (Step S306). The reconstruction unit 34e reconstructs an X-ray CT image from the expanded data thus corrected by performing back projection processing (Step S307), and the processing is terminated.

As described above, in the third embodiment, by performing back projection of the expanded data in which the compression distortion is nearly uniform or the expanded data on which the correction processing is performed, an image is reconstructed. In other words, the inverse transformation explained in the second embodiment can be omitted in the third embodiment. In the third embodiment, however, the transformation unit 17b needs to perform logarithmic transformation unique to the system performed by the preprocessing unit 34c or to perform approximate transformation that approximates the logarithmic transformation unique to the system performed by the preprocessing unit 34c.

In the third embodiment, it is possible to transmit compressed data of X-ray detection data with which the image quality of a tomographic image is not degraded. Therefore, neither a high-speed transmission system nor a device that stores therein a large volume of data is required for reconstruction of an accurate tomographic image.

Figure 17:
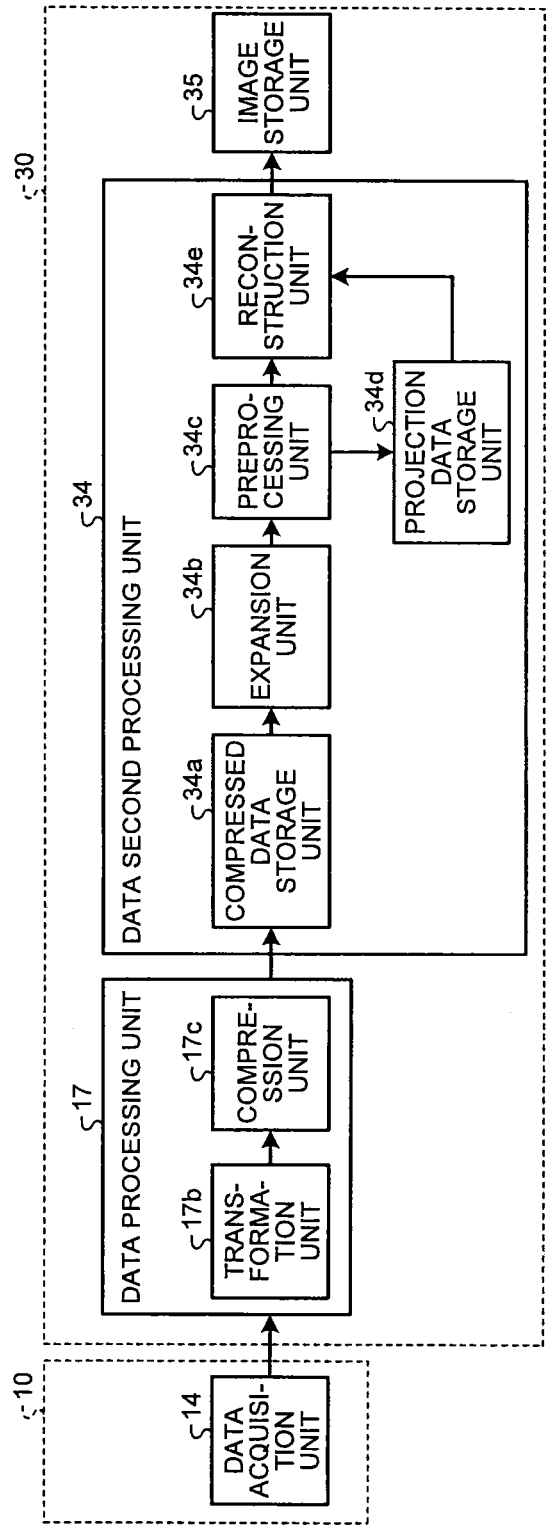
FIG. 17 is a schematic for explaining a modification of the third embodiment.

The explanation has been made of the case where the transformation processing and the compression processing of the X-ray detection data are performed by the gantry apparatus 10. Alternatively, in the third embodiment, the transformation processing and the compression processing of the X-ray detection data may be performed by the console device 30. FIG. 17 is a schematic for explaining a modification of the third embodiment.

As illustrated in FIG. 17, in the modification of the third embodiment, the data processing unit 17 including the transformation unit 17b and the compression unit 17c is provided to the console device 30. The transformation unit 17b illustrated in FIG. 17 uses a transform function for X-ray detection data received from the gantry apparatus 10 to generate transformed data. The compression unit 17c then performs compression processing on the transformed data, thereby generating compressed data.

In the modification illustrated in FIG. 17, a device that stores therein data need not have large storage capacity in at least the console device 30 for reconstruction of an accurate tomographic image.

Figure 18:
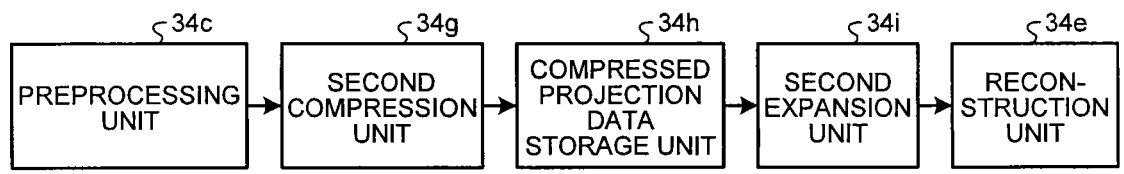
FIG. 18 is a schematic for explaining a modification of the first to the third embodiments.

In the first to the third embodiments, the explanations have been made of the case where X-ray detection data or transformed data generated from X-ray detection data is compressed and compressed data thus obtained is stored. However, in the first to the third embodiments, data yet to be reconstructed may be further compressed to be stored. FIG. 18 is a schematic for explaining a modification of the first to the third embodiments.

As illustrated in FIG. 18, in the modification of the first to the third embodiments, a second compression unit 34g, a compressed projection data storage unit 34h, and a second extension unit 34i are provided between a preprocessing unit 34c and a reconstruction unit 34e. The second compression unit 34g compresses data output from the preprocessing unit 34c, that is, data just prior to being used for reconstruction, and stores the data thus compressed in the compressed projection data storage unit 34h as compressed projection data. The compression processing performed by the second compression unit 34g is normal compression processing with no specific control of the quantization level or the like.

In reconstruction of an image, the second expansion unit 34i reads the compressed projection data from the compressed projection data storage unit 34h, and performs expansion processing to restore projection data. The reconstruction unit 34e performs back projection of the projection data, thereby reconstructing an image. According to the modification illustrated in FIG. 18, it is possible to reduce storage capacity required for the conventional projection data storage unit 34d.

In the first to the third embodiments, the explanation has been made of the case where compression is performed by DPCM. Alternatively, the first to the third embodiments can be applied to the case where compression is performed by wavelet transform and discrete cosine transform, for example.

The radiation detection data processing method explained in the first to the third embodiments may be applied to a CT apparatus that acquires radiation detection data from the subject P, transforms the data thus acquired logarithmically, and reconstructs an image by performing back projection besides the X-ray CT apparatus. For example, the radiation detection data processing method explained in the first to the third embodiments may be performed by a nuclear medicine imaging apparatus, such as a single photon emission computed tomography (SPECT) apparatus and a positron emission computed tomography (PET) apparatus.

A nuclear medicine imaging apparatus uses a detector to acquire detection data of gamma rays emitted from a radiopharmaceutical administered to a subject and selectively delivered into a body tissue of the subject. The nuclear medicine imaging apparatus transforms the gamma-ray detection data logarithmically to generate projection data, and reconstructs a nuclear medicine image (e.g., a SPECT image and a PET image) in which biodistribution of the radiopharmaceutical administered to the subject is depicted from the projection data.

In other words, if the nuclear medicine imaging apparatus performs compression processing and expansion processing of the gamma-ray detection data, the quality of a tomographic image is degraded because distribution in compression distortion increases depending on signal intensity similarly to the X-ray CT apparatus. To address this, by applying the radiation detection data processing method explained in the first to the third embodiments to the gamma-ray detection data, it is possible to prevent image degradation of a tomographic image due to compression processing. Furthermore, the radiation detection data processing method may be applied to a CT apparatus used for non-destructive testing.

The radiation detection data processing method may be performed by a radiation detection data processing apparatus provided separately from a CT apparatus. In other words, the radiation detection data processing method may be performed by reception of radiation detection data acquired by a CT apparatus in a radiation detection data processing apparatus having at least a compression function of the data processing unit 17.

As described above, according to the first to the third embodiments, it is possible to prevent image degradation of a tomographic image due to compression processing.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation detection data processing apparatus comprising:
a data acquisition unit configured to acquire a radiation detection data from a detector detecting radiation; and
a data processing unit configured to generate compressed data from the radiation detection data, compression distortion in a data generated from the compressed data to be used for reconstruction of a tomographic image is nearly uniform independently of a signal value, wherein
the data processing unit comprises a compression unit configured to generate the compressed data based on the radiation detection data by using a quantization level at which compression distortion included in a lower signal value is smaller than compression distortion included in a higher signal value.

2. A radiation detection data processing apparatus comprising:
a data acquisition unit configured to acquire a radiation detection data from a detector detecting radiation; and
a data processing unit configured to generate a compressed data from the radiation detection data, compression distortion in a data generated from the compressed data to be used for reconstruction of a tomographic image is nearly uniform independently of a signal value, wherein
the data processing unit comprises:
a transformation unit configured to perform logarithmic transformation or approximate transformation that approximates the logarithmic transformation on the radiation detection data to generate transformed data; and
a compression unit that compresses the transformed data to generate the compressed data.

3. The apparatus according to claim 1, further comprising:
an expansion unit configured to generate expanded data by expanding the compressed data; and
a reconstruction unit configured to perform back projection of projection data generated by transforming the expanded data logarithmically to reconstruct a tomographic image.

4. The apparatus according to claim 2, further comprising:
an expansion unit configured to generate expanded data by expanding the compressed data;
an inverse transformation unit configured to performs inverse transformation of transformation performed by the transformation unit on the expanded data to generate inverse transformed data; and a reconstruction unit configured to perform back projection of projection data generated by transforming the inverse transformed data logarithmically to reconstruct a tomographic image.

5. The apparatus according to claim 2, farther comprising:
an expansion unit configured to generate expanded data by expanding the compressed data; and
a reconstruction unit configured to perform back projection of the expanded data to reconstruct a tomographic image.

6. The apparatus according to claim 3, further comprising:
a compressed data storage unit configured to store therein the compressed data, wherein
the expansion unit is configured to perform expansion processing on compressed data stored in the compressed data storage unit.

7. The apparatus according to claim 4, further comprising:
a compressed data storage unit configured to store therein the compressed data, wherein
the expansion unit is configured to perform expansion processing on the compressed data stored in the compressed data storage unit.

8. The apparatus according to claim 5, further comprising:
a compressed data storage unit configured to store therein the compressed data, wherein
the expansion unit is configured to perform expansion processing on the compressed data stored in the compressed data storage unit.

\* \* \* \* \*